United States Patent
Grady (10) Patent No.: US 7,300,205 B2
(45) Date of Patent: Nov. 27, 2007

(54) ANGIO CAPABLE PORTABLE X-RAY FLUOROSCOPY UNIT WITH SLIDING C-ARM AND VARIABLE PIVOT

(76) Inventor: John K. Grady, 43 Slough Rd., Harvard, MA (US) 01451

( * ) Notice: Subject to any disclaimer, the term of this patent is extended or adjusted under 35 U.S.C. 154(b) by 0 days.

(21) Appl. No.: 11/563,260

(22) Filed: Nov. 27, 2006

(65) Prior Publication Data
US 2007/0121790 A1    May 31, 2007

Related U.S. Application Data

(60) Provisional application No. 60/739,712, filed on Nov. 25, 2005.

(51) Int. Cl.
H05G 1/06 (2006.01)
(52) U.S. Cl. ........................ 378/198; 378/197
(58) Field of Classification Search ......... 378/195–198
See application file for complete search history.

(56) References Cited

U.S. PATENT DOCUMENTS

| | | |
|---|---|---|
| 4,150,297 A | 4/1979 | Borggren |
| 4,209,706 A | 6/1980 | Nunan |
| 4,481,656 A | 11/1984 | Janssen et al. |
| 4,541,293 A | 9/1985 | Caugant et al. |
| 4,868,845 A | 9/1989 | Koropp |
| 4,887,287 A | 12/1989 | Cobben |
| 4,918,716 A | 4/1990 | Hahn |
| 4,955,046 A | 9/1990 | Siczek et al. |
| 5,014,293 A | 5/1991 | Boyd et al. |
| 5,050,204 A * | 9/1991 | Siczek et al. ............... 378/197 |
| 5,052,036 A | 9/1991 | Grady |
| 5,226,069 A | 7/1993 | Narita |
| 5,515,416 A | 5/1996 | Siczek et al. |
| 5,521,957 A | 5/1996 | Hansen |
| 5,583,909 A | 12/1996 | Hanover |
| 5,901,200 A | 5/1999 | Krause |
| 6,325,537 B1 | 12/2001 | Watanabe |
| 6,428,206 B1 * | 8/2002 | Watanabe ................... 378/197 |
| 7,018,097 B2 | 3/2006 | Schmitt |
| 7,129,666 B2 | 10/2006 | Bauer et al. |
| 7,168,855 B2 * | 1/2007 | Engstrom et al. ........... 378/197 |

* cited by examiner

Primary Examiner—Hoon Song
(74) Attorney, Agent, or Firm—Donald S. Holland, Esq.; Holland & Bonzagni, P.C.

(57) ABSTRACT

An "Angio Capable Portable X-Ray Fluoroscopy Unit with Sliding C-Arm and Variable Pivot Point" is disclosed. It is a new Portable C-Arm x-ray system for fluoroscopy (e.g., angio fluoroscopy) that permits head-to-foot, or cranio-caudal, angulation without appreciable degradation or rotation of the recorded image in the segment of possible views most desired to be used for cardiac angiography, generally between a vertical beam and 60 degrees to the patient's left side from vertical. Applicant's preferred embodiment comprises an portable x-ray device of the type having a C-arm which "slides" through a fixed C-slider housing or sleeve mounted onto a portable base, wherein: the C-slider housing is mounted onto the portable base through a rotatable tilt bearing, and the rotation axis of the bearing and fixed sleeve can be repositioned, within an arcuate slot in the base, from approximately horizontal, when the x-ray beam is vertical, to between approximately 60 degrees and 40 degrees below horizontal in a vertical plane.

8 Claims, 7 Drawing Sheets

ANGIO CAPABLE PORTABLE X-RAY FLUOROSCOPY UNIT WITH SLIDING C-ARM AND VARIABLE PIVOT

RELATED APPLICATION

This Utility application is based upon a Provisional Application, Ser. No. 60/739,712, filed Nov. 25, 2005 by the same Applicant. Applicant claims the benefit of priority from that earlier application.

FIELD OF THE INVENTION

The present invention generally relates to support and positioning apparatus for x-ray equipment. More particularly, the invention relates to portable x-ray units with sliding C-shaped arms.

BACKGROUND OF THE INVENTION

Fluoroscopy is a process for obtaining continuous, real-time images of an interior area of a patient via the application and detection of penetrating x-rays. Put simply, x-rays are transmitted through the patient and converted into visible spectrum light by some sort of conversion mechanism (e.g., x-ray-to-light conversion screen and/or x-ray image intensifier). Subsequently, the visible light is captured by a video camera system (or similar device) and displayed on a monitor for use by a medical professional. More recently, a solid-state pixelized flat panel is used for this purpose. Typically, this is done to examine some sort of ongoing biological process in the human body, e.g., the functioning of the lower digestive tract or heart.

Currently, most fluoroscopy is done using x-ray image intensifiers. These are large, vacuum tube devices (i.e., akin to a CRT or conventional television) that typically receive the x-rays in an input end, convert the x-rays to light and then electron beams, guide, accelerate, and amplify the electron beams via internal electrodes, and convert the electron beams to a minified visible image at the device's output end. An example of an x-ray image intensifier is shown in U.S. Pat. No. 5,773,923 to Tamagawa (see FIGS. 1 and 2 and accompanying description).

In designing x-ray support apparatuses, the x-ray device should ideally be positionable for use anywhere around the periphery of a patient in three dimensions (i.e., the X-, Y-, Z-planes). More specifically, it is typically desirable to utilize spherical angulation, where x-rays can be directed from any loci on an imaginary sphere centered on the patient to an isocenter of the x-ray device. (The isocenter is the point of intersection of an axis defined by the x-ray source and receptor and the axis of angulation, i.e., the axis of device rotation.) Other factors to take into account include: maintaining the x-ray beam normal to the x-ray receptor; the size of the examination room, and the room's ability to accommodate large devices; unrestricted access to the patient, especially around the head area; minimizing control complexity and/or the need for computer image correction or manipulation; and, as always, cost.

Most current x-ray device support apparatuses utilize either a parallelogram-shaped construct or a combination of C-, U-, and/or L-shaped arms for x-ray device positioning and (ideally) spherical angulation. An example of the former is shown in U.S. Pat. No. 3,892,967 to Grady et al. ("Grady '967"). In Grady '967, an x-ray source 23 and receptor 22 are positioned with respect to a patient P by way of an angularly-adjustable, pivoting, rotating parallelogram 3, 5, 8, 9. This achieves 360 degrees rotation coverage about the patient P, by virtue of the parallelogram being rotatable about shaft 2, and 55 degrees of head/foot tilt (the arms 8, 9 can be moved in and out.) Thus, the device basically moves in an unrestricted way on the surface of a sphere about the patient, and the x-ray image itself inherently always remains "upright" irrespective of the compound angles used. However, to cover from head to foot on a six foot tall patient, the "throat depth" (clearance) of the support apparatus has to be over six feet. This makes the support apparatus at least ten to twelve feet long, plus the patient tabletop has to travel at least six feet, which means it must be eight to nine feet long. Thus, the entire system is almost twenty feet long, necessitating a twenty-eight or thirty foot long room, which might cause architectural problems.

Because parallelogram-based devices are so bulky, various C-arm based devices have been developed over the years. However, large C-arms are difficult to balance (e.g., a parallelogram can be an entirely mechanically-balanced device), since the entire mass of the C-shaped structure is offset to one side. Accordingly, these have primarily taken the form of a simple, light, balanced, C-shaped arm which holds the x-ray source at one end and the receptor at the other end. The C-shaped arm slides in a journal, and is positionable by way of one or more pivoting arms attached to the journal. Such devices can deliver most of the angular coverage of a parallelogram in a smaller space, but typically have several severe, inherent problems, such as the inability to carry heavy equipment without dangerous power-driven operation, and if the C-arm slides in the journal, the image will rotate due to an interaction of the two axes. Some parts of the spherical view become inaccessible.

With existing C-arm based devices, as the axis of the x-ray beam approaches the horizontal, rotating the horizontal axis only serves to rotate the image, without changing the viewing angle. This results in zero image rotation with a vertical beam, and 100 percent rotation (only) at a horizontal beam. In between 0 degrees and 90 degrees the x-ray beam/positioner angular relationship is complex, and the two rotation axes interact. The result is a tilted image as viewed on the x-ray image screen. This effect can be compensated for by either mechanically rotating the x-ray receptor (and also the source collimator if a square x-ray field is utilized) according to a pre-programmed code, or by implementing an "image de-rotation" scheme where the image, as stored electronically, is manipulated by digital means. However, such systems are expensive, and can ultimately degrade the image. Some angulations critical to cardiology are no longer achievable once the arm is slid in its sliding bearing (i.e., its outer sleeve).

There have been numerous variations in the design and construction of C-arm based x-ray gantries, but two main divisions are apparent: types where the horizontal C-arm axle comes at the patient from the left side, and types where the C-arm axle comes over the patient's head.

For an axle or C-arm mount that is horizontal, approaching the patient from the left side is the ideal orientation, as the head end of the patient is then accessible for anesthesia, nursing care, etc. The tilt range of the "sliding C", and hence the efficacy of the equipment, in that arrangement is unfortunately reduced as the x-ray beam approaches horizontal, as mentioned above.

The easiest way to visualize this is to note that when the x-ray beam is vertical ("upwards"), any rotation of the generally horizontal main axle of the C-arm mount also predictably tilts the x-ray beam angle a like amount. For example, a 30-degree rotation of the main axle tilts the x-ray beam angle 30 degrees. As long as the main axle or pivot makes close to a right angle (90 degrees) with the x-ray beam, the overall goal is achieved.

However, once the C-arm (a.k.a. the "C") is "slid" in its mount sleeve, the difficulty appears. To go to the extreme, if the C is slid by 90 degrees from its vertical position, where the beam was vertical, to a new horizontal position with the beam is also horizontal, and then the main pivot is rotated by the same 30 degrees, there is no change in x-ray beam angle at all. The 30 degree rotation of the main axle only serves to rotate the image receptor, which rotates the displayed image.

Two situations result with the C slid to the horizontal beam position:

1) no head-to-foot, or cranio-caudal, angulation is possible; and 2) the image rotates on the viewing screen if the axle is turned.

For intermediate positions along the sliding C motion, a mix of the two situations appears, and they interact in a complex way. The essence of the situation is that for x-ray beams near lateral, with the C on the left side of the patient, there is very little cranio caudal angulation available and image rotation is severe.

These problems led to the "parallelogram" support and positioning apparatus for x-ray equipment disclosed in the Grady '967 patent, mentioned above, issued in 1975 to John K. Grady (the present Applicant) and David B. Rice. That "parallelogram" apparatus has none of the above issues, but obstructs the head of the patient and requires a long room. The image on a parallelogram does not rotate at all for all spherical views.

A first prior solution for the C-arm construction is to move the C-arm to the head end permanently. However, that obstructs the head end. It also gives very limited coverage of the patient, as the C-arm radius is limited by the floor and the center point must be inside the patient. Consequently, the patient's head will strike the C-arm interior diameter before the beam is in the pelvic area.

A second prior art solution is to mount the C-arm on a third axis pivot, which allows it to be moved from the left side to the head end of the patient, depending on clinical requirements. There are many existing variations along this theme, with floor and ceiling pivots, dual third axis pivots generating on offset, etc. All suffer from the complexities of a third pivot, coordinating that pivot to the other two, and adding a new source of image rotation that interacts with the other two in a complex way. With the recent advent of software based 3-D image reconstructions, the impact of image rotation or shifts is really severe, often becoming a limiting factor in the data integrity.

These problems can be solved for a stationary catheterization ("cath") lab with a different approach—see U.S. Pat. No. 6,789,941 ("Grady '941"), issued Sep. 14, 2004 to John K. Grady. Grady '941 describes a C-shaped arm with a pivot fixed at 90 degrees to the beam, the whole thing traveling inside an arc. Note that there is no sliding mount or sleeve on the C-arm mount at all; that deletion eliminates image rotation. The "axle pivot" (equivalent) is actually moving with the C-arm, always at 90 degrees to the main beam, a critical design differentiator.

Application of These Concepts to a Portable C-Arm Unit for Angiography

All "Portable C-arm" x-ray systems sold to date combine a sliding C-arm type of construction with a generally horizontal axle or an axle fixed at some compromise angle, so the problem of interacting angular capabilities described above are the norm. This prevents effective use of the systems for cardiac angiography, which requires steep angulation in both directions, with a beam close to horizontal.

Some attempts to overcome this have included permanently offsetting the normally horizontal axle pivot, to a fixed angle below horizontal, and moving the sliding attachment point or C-arm "sleeve" to a position generally about 45 degrees below horizontal. This design was in fact originally less concerned with angular capabilities, than with providing room for the image tube and camera to "tuck in" in line with the horizontal axis, as a lateral beam without head-to-foot tilt is a required capability, especially in orthopedic surgery. Having the "grabbing sleeve" right at the horizontal axis will cause packaging problems that conflict with a horizontal beam—the "sleeve" and image tube try to occupy the same space. This also prevents the image intensifier and camera from passing the sleeve, wherever the sleeve is positioned.

Applicant tried to apply the "C-arm within an arc" concept of U.S. Pat. No. 6,789,941 to a portable (wheeled) device. However, Applicant soon recognized that the required vertical height of the arc (over 7 feet) and its massive size precluded packaging that equipment, as is, on a portable or wheeled device.

Accordingly, the primary object of the present invention is to provide a Portable C-Arm x-ray system for angio fluoroscopy that permits head-to-foot, or cranio-caudal, angulation without appreciable degradation or rotation of the recorded image in the segment of possible views most desired to be used for cardiac angiography, generally between a vertical beam and 60 degrees to the patient's left side from vertical. That corresponds to a horizontal pivot and to a pivot 60 degrees below horizontal, as the pivot must be kept at 90 degrees to the beam, or close to it, to avoid the problems described above.

It is a more specific object to provide a Portable C-Arm system that utilizes the sliding C-arm concept, as is well known for many other uses, but which adds to that a limited range of motor driven, variable location of the usually horizontal axle pivot, giving results similar to U.S. Pat. No. 6,789,941, but keeping a sliding C-arm mount for other customary uses.

The above and other objects of this invention will become more readily apparent upon reading the following descriptions and viewing the accompanying drawings.

SUMMARY OF THE INVENTION

An "Angio Capable Portable X-Ray Fluoroscopy Unit with Sliding C-Arm and Variable Pivot Point" is disclosed. This new Portable C-Arm system keeps the well-known sliding C concept, but improves its efficacy. The novel system overcomes the prior limited range of Portable C-Arm systems by adding a motor driven, variable location of the axle pivot, giving results similar to U.S. Pat. No. 6,789,941 ("Grady '941"), issued Sep. 14, 2004 to the current Applicant, John Grady, but keeping a sliding C-arm mount.

In the preferred embodiment, Applicant's invention comprises a standard Portable C-arm apparatus (e.g., the apparatus of Grady '941) having a C-arm which slides through a fixed C-sleeve mount (a.k.a. "C-slider housing") via a drive sprocket, improved as follows: the sleeve is mounted onto a portable base through a rotatable tilt bearing, and a rotation axis of the bearing and fixed sleeve can be repositioned, within an arcuate slot in the base by a motor, from approximately a horizontal position, when the x-ray beam is vertical, to a position between approximately 60 degrees and 40 degrees below horizontal in a vertical plane.

The repositioning provides a head-to-foot, or cranio-caudal, angulation without appreciable degradation or rotation of the recorded image in the segment of possible views most desired to be used for cardiac angiography.

DETAILED DESCRIPTION OF THE PREFERRED EMBODIMENT

Referring to FIGS. 1-7, Applicant has disclosed a preferred embodiment of an "Angio Capable Portable X-Ray Fluoroscopy Unit with Sliding C-Arm and Variable Pivot Point." This new Portable C-Arm system keeps the well-known sliding C concept, but improves its efficacy. The novel system overcomes the prior limited range of Portable C-Arm systems by adding a motor driven, variable location of the axle pivot, but keeping a sliding C-arm mount.

As with U.S. Pat. No. 6,789,941 ("Grady '941") issued Sep. 14, 2004 to the current Applicant, John Grady (hereby incorporated by reference), the drawings for Applicant's present embodiment depict a portable C-arm support apparatus 100. The portable C-arm support includes a large radius C-arm (preferably made of carbon fiber) 104 having slide travel rails (e.g., 106) on opposite sides of the C. These slide rails, together with a mid-length of the C-arm 104, can travail within an outer, shorter C-sleeve (a.k.a. "C-slider housing") 108. The rails are driven by sprockets (not shown) turned by an electric motor (not shown).

One end portion of the C-arm 104 and its slide rails (e.g., 106) are placed behind an image receptor assembly 114 centerline 116. That way, the C-arm can pass by the image receptor assembly 114 without interfering with (i.e., hitting) the assembly.

The C-arm projection itself, at either end, or just the end nearest the image receptor, contains balance weights at 116. These weights offset the unbalancing moment of the C-Arm mass and source assembly to allow manual motion of the slide axis. These counterweights are similar to the technique found in Grady '941.

Applicant's preferred embodiment contains the same structure found in Grady '941, with the following exceptions. The C-arm of Grady '941 can be moved only in a stationary arc along the X-Y plane (i.e., in a single plane), within a C-sleeve whose location is fixed. Applicant's current invention preferably includes: a rotatable tilt bearing means 120 for pivoting the arc (and C-slider) in a Z-plane around a pivot axis (a.k.a. C-slider axis) 122; and a sliding pivot point means 124 for repositioning the tilt bearing means 120, and pivot axis 122, in the X-Y plane along an arcuate path. The tilt bearing means 120 and the sliding pivot point means 124 combine to create extreme compound angles related to cardiac catheterization ("cath").

In simpler terms, Applicant's preferred embodiment can be thought of as a portable x-ray device of the type having an x-ray source 102, an image receptor assembly 114, and a C-arm 104 which slides through a fixed C-slider housing 108 mounted onto a portable base 126, the improvement comprising: the C-slider housing 108 is mounted onto the portable base 126 through the rotatable tilt bearing means 120 for pivoting the arc (and C-slider housing 108) in a Z-plane around C-slider rotational axis 122; and, the C-slider rotational axis 122, plus C-slider 108, can be repositioned along an arcuate slot 130 (in the base 126) by the sliding pivot point means 124 from approximately a horizontal position to a position between approximately 60 degrees and 40 degrees below horizontal in a vertical plane.

Sliding pivot point means 124 preferably includes an arcuate pivot carriage guide track 132, aligned with slot 130 and mounted within the base 126. Track 132 and slot 130 have similar arcuate lengths. Those lengths are shown as 60 degrees.

Track 132 has upper and lower surfaces, plus closed ends, that form an internal curved housing for a C-slider pivot carriage 134. Carriage 134 has guide rollers for sliding the carriage 134 within the confines of the guide track housing.

Figure 1:
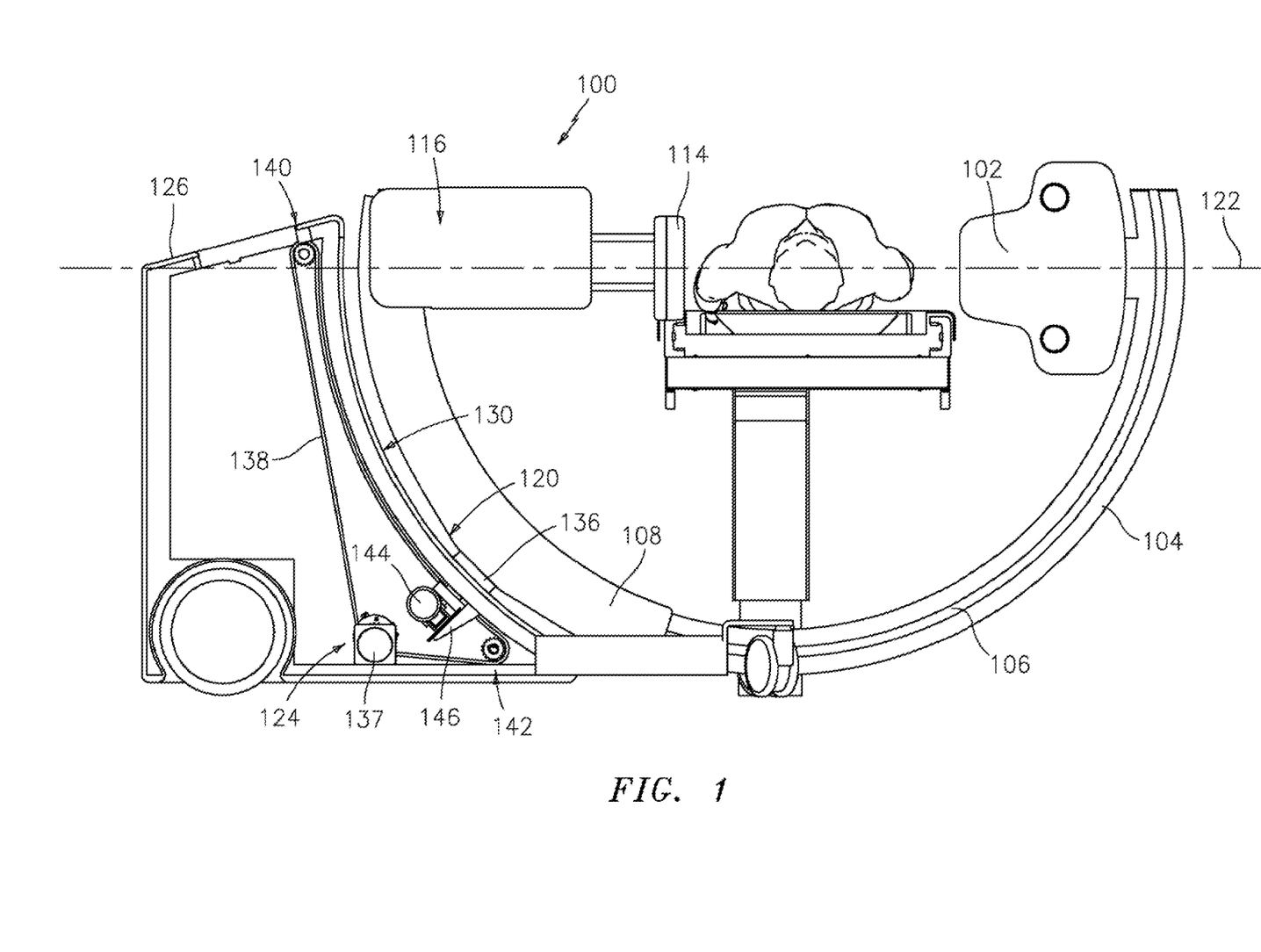
FIG. 1 is a side view of an "Angio Capable Portable X-Ray Fluoroscopy Unit with Sliding C-Arm and Variable Pivot Point," constructed in accordance with the present invention, depicting a Portable C-Arm device with an angled slider pivot axis set at 45 degrees below horizontal and a sliding C at a horizontal position.
Figure 2:
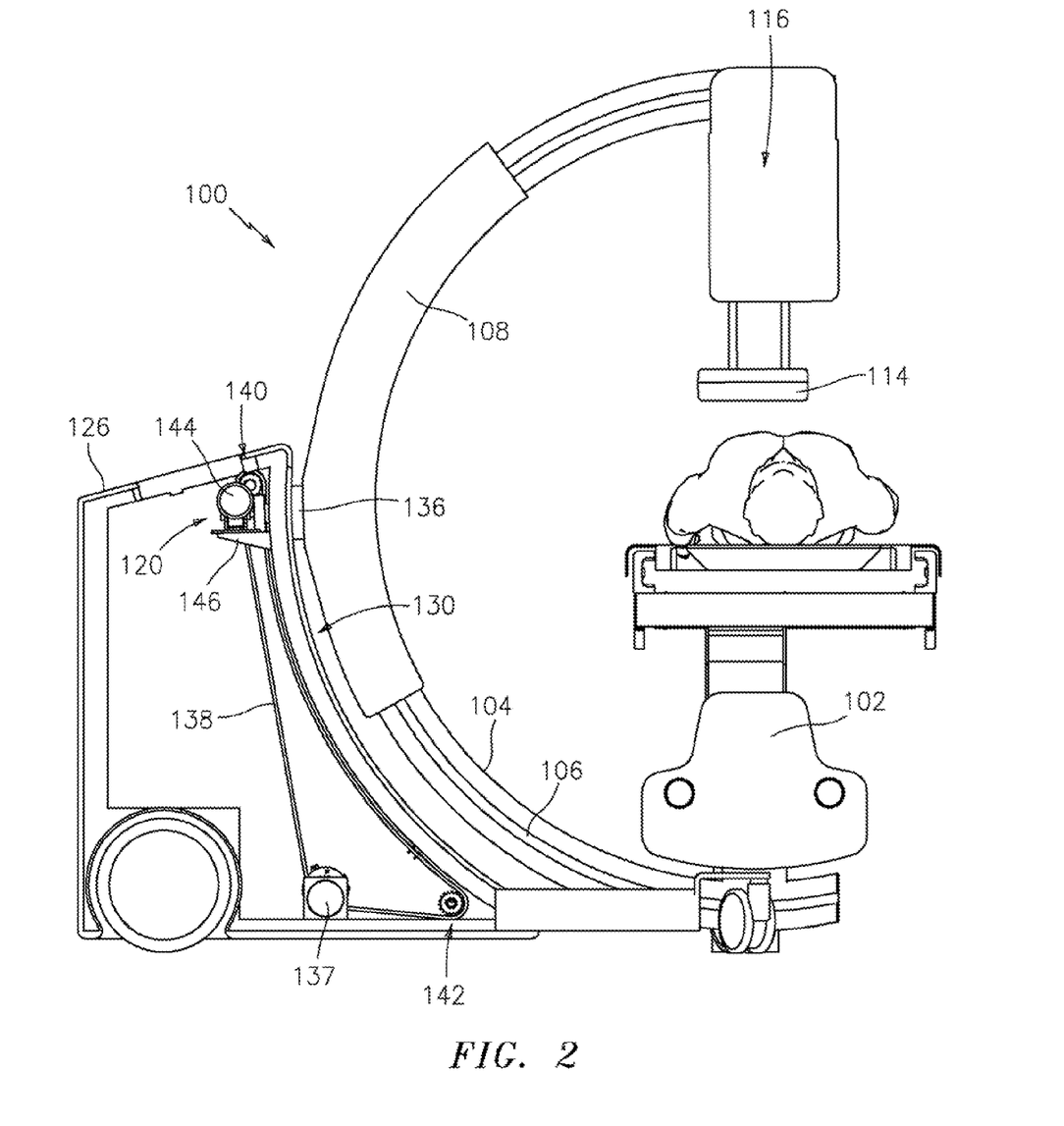
FIG. 2 is another side plan view of the Portable C-Arm device with the slider pivot axis raised to 0 degrees (horizontal) from its FIG. 1 orientation and the C slid or translated to a vertical position.
Figure 3:
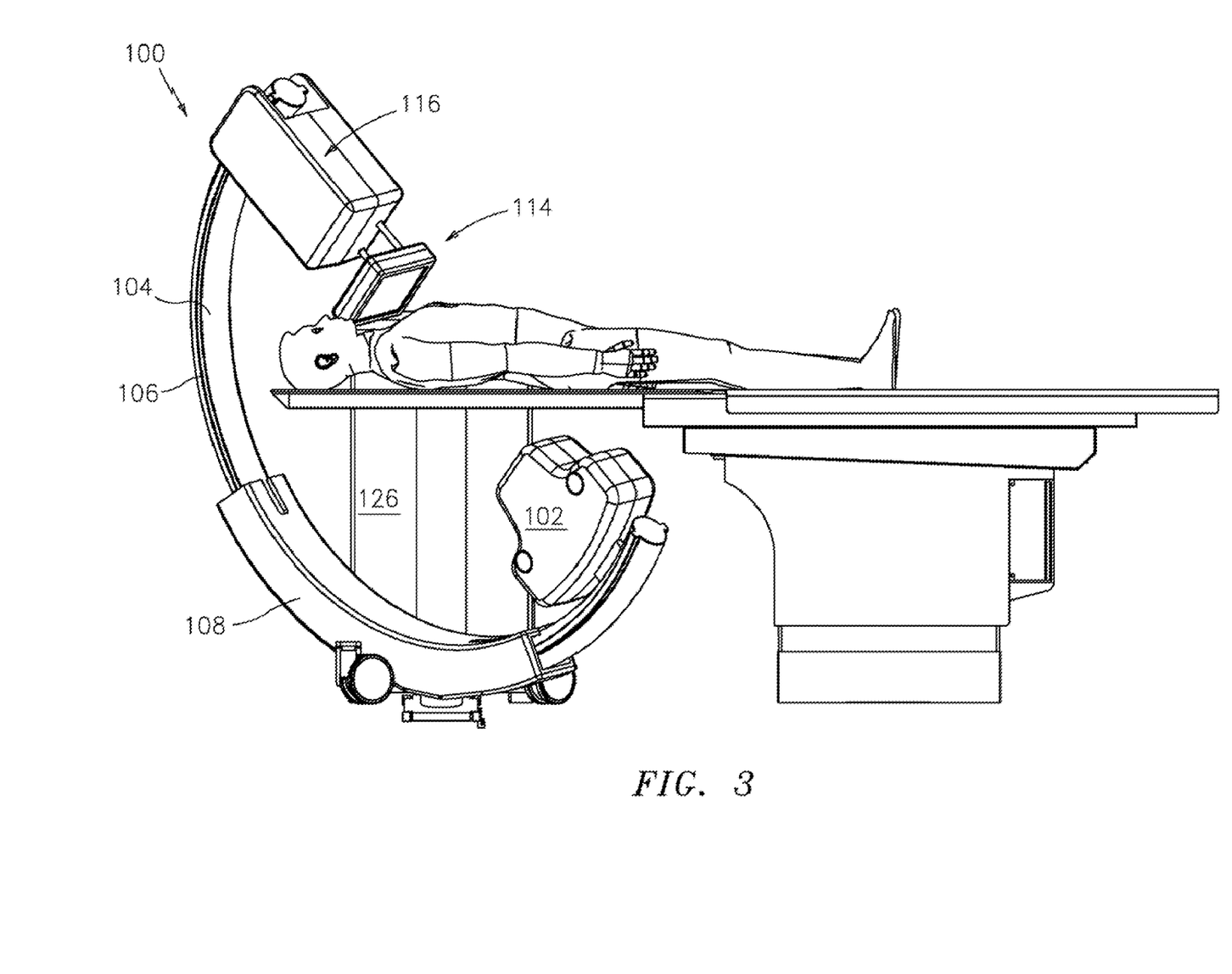
FIG. 3 is a front plan view of the Portable C-Arm device at a cranio-caudal orientation.
Figure 4:
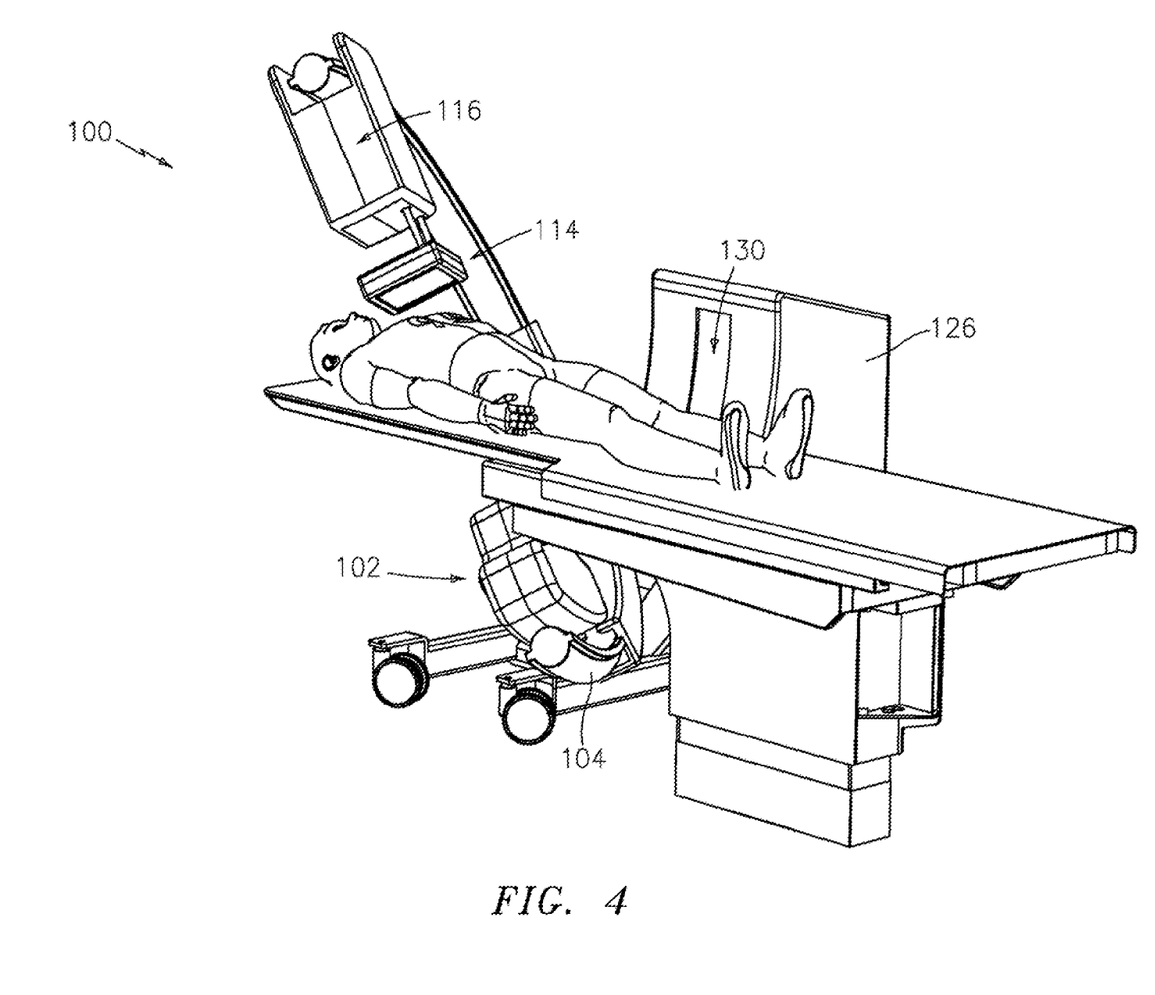
FIG. 4 is a perspective view of the Portable C-Arm device in its FIG. 3 orientation.
Figure 5:
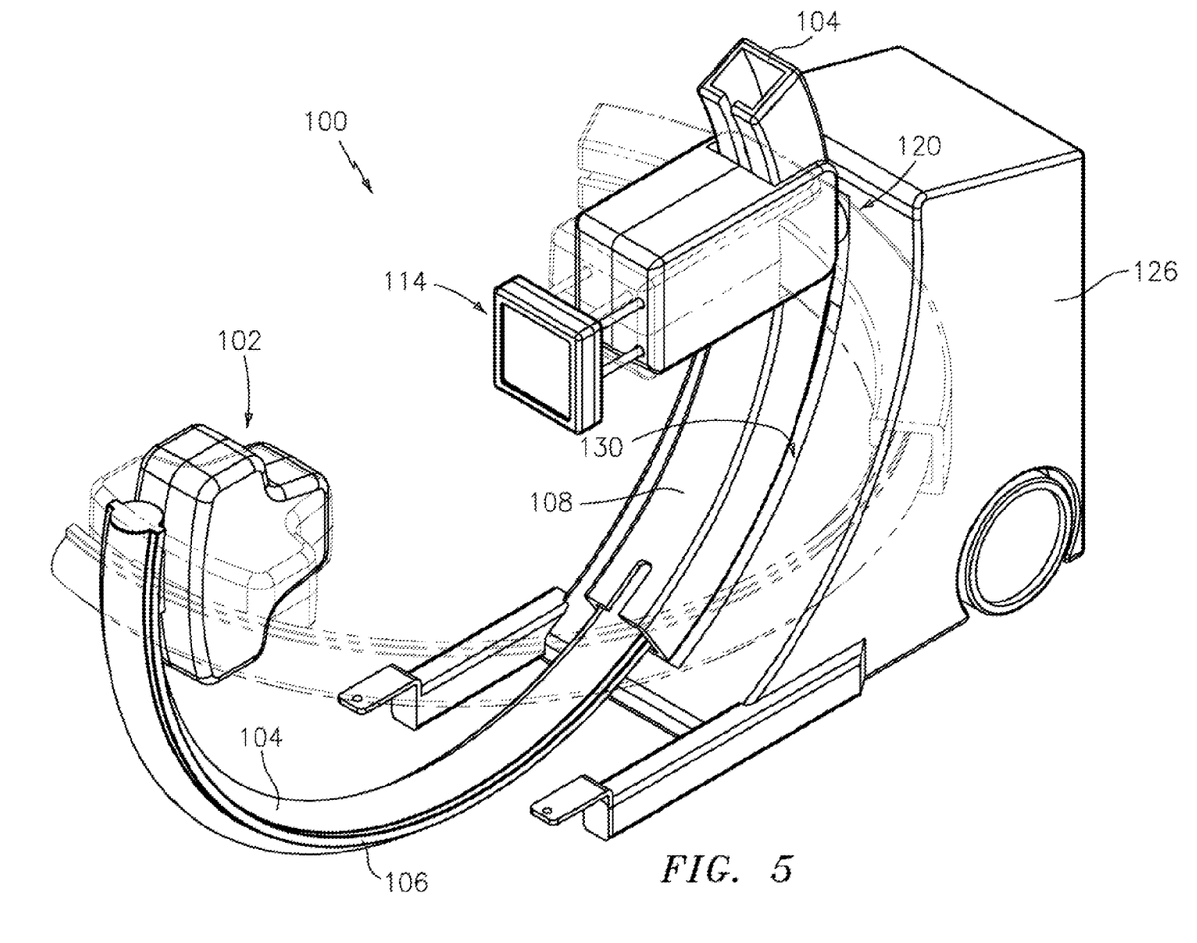
FIG. 5 is a perspective view of the Portable C-Arm x-ray device with the slider pivot axis set at 0 degrees (horizontal) and the housing having been rotated, along that axis, from a vertical position (shown in phantom) to horizontal.
Figure 6:
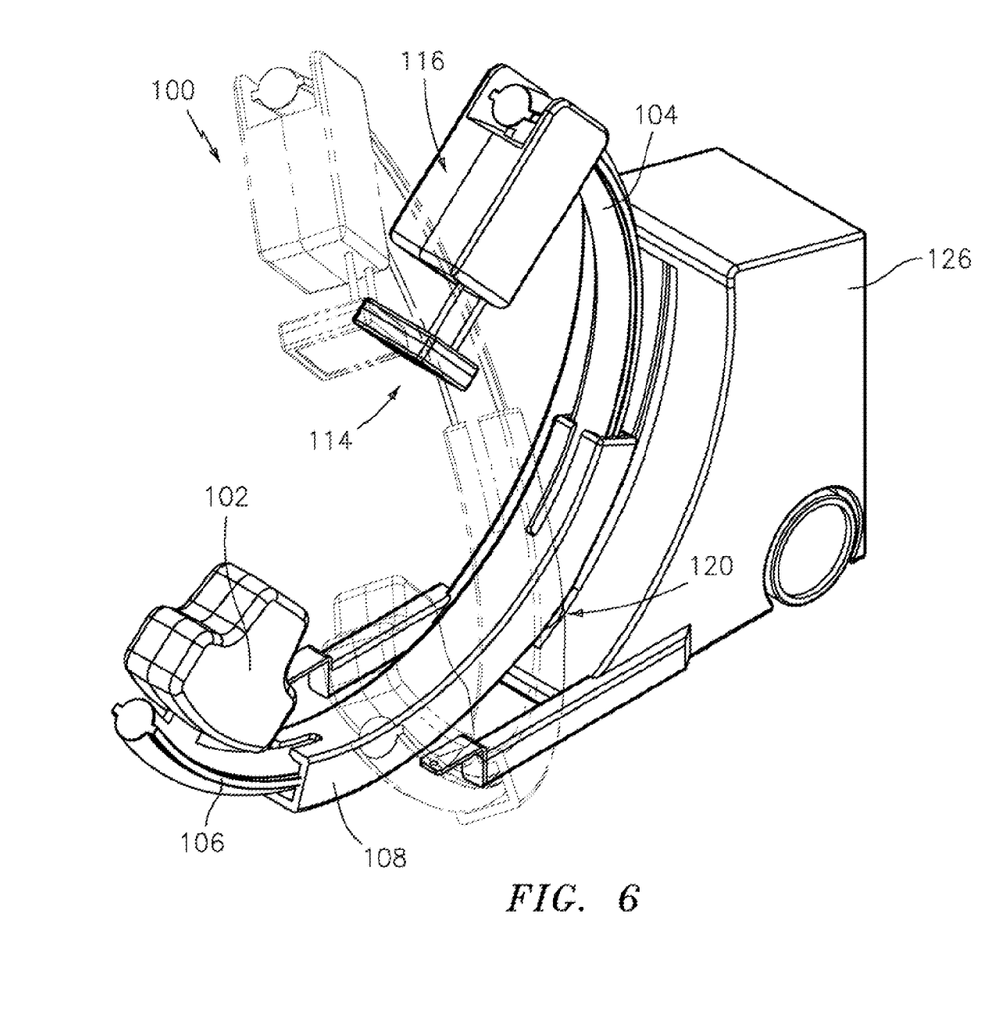
FIG. 6 is a perspective view of the Portable C-Arm x-ray device with the slider pivot axis set at 60 degrees below horizontal and the housing having been rotated from a cranio-caudal orientation (shown in phantom) at 45 degrees to 0 degrees.
Figure 7:
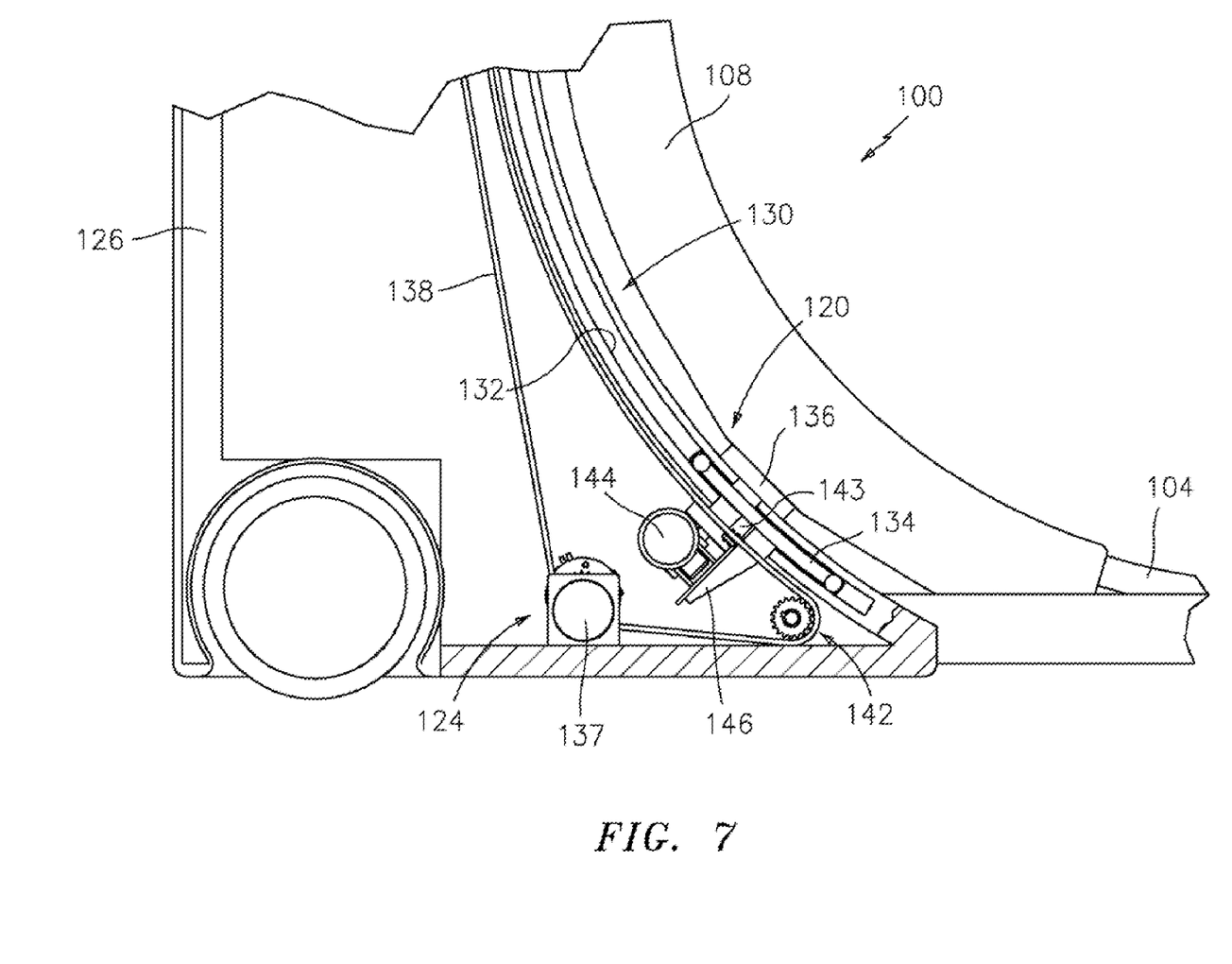
FIG. 7 is a perspective view of a portable base, with a side cover removed (as in FIGS. 1 and 2), showing portions of a rotatable tilt bearing means and a sliding pivot point means inside the base.

As best shown in FIG. 7, carriage 134 is attached to the C-slider 108 by a rotatable tilt bearing 136 that rides atop a slot (not shown) in guide track 132. A drive gearmotor 137 selectively slides the carriage 134 and C-slider 108 by a drive chain 138. The drive chain 138 rides over sprockets 140 and 142, and is fixed to the underside of the carriage by a set screw 143.

As best shown in FIG. 7, tilt bearing means 124 preferably comprises a reversible drive motor 144 removably attached to the rotatable tilt bearing 136 by any suitable means, such as pinning. Motor 144 preferably has a drive shaft which extends through a slot in the bottom of the track 132 housing, up though a hole in the carriage 134. Motor 144 preferably is mounted on a tab 146 that runs in a lower slot of the guide track between the guide rollers. Other mounts and attachments would also do. A user (not shown) can utilize the motor to selectively rotate C-slider housing 108 about the C-slider axis 122.

Applicant has realized that the need for extreme compound angles (related to cardiac cath) actually occur only in a series of views generally encompassed by the receptor being on the left side of the patient, rotated about 50 to 60 degrees around the patient, and tilted about 35-40 degrees toward the head of the patient. This "compound angle" will best display the coronary arteries of the heart, by having the x-ray beam impinge on them approximately orthogonal to them as they lie in their normal anatomical position. This view is critical to doing accurate measurements, etc., as when placing coronary stents.

To accomplish these views, it is only necessary to keep the pivot of the axle of the C orthogonal for only the limited range of possible views needed for a cardiac examination. The invention is preferably used with a patient table having a slidable top. That enables the patient to be slid within the confines of the C-arm (i.e., interior of C-arm "diameter") and withdrawn after using the equipment.

The reason for Applicant's sliding mount is to allow mounting the entire system on the cart-like base 126. This base does not need an outer arc track higher than the horizontal beam. Yet this is capable of mimicking the large system in its cardiac abilities for angles between a vertical beam and a beam approximately rotated 60 degrees to the patient's left. It does this by moving the axle pivot from about horizontal (when the useful x-ray beam is vertical) to about 60 degrees (or more) below horizontal, when the main beam is rotated 60 degrees to the left (looking from the patient's feet).

The moving axle pivot replaces the prior "sleeve" or sliding motion in this critical area, enabling cardiac cath related angles to be achieved on a "portable" C-arm, without using the "sliding" motion; yet the sliding motion remains for other uses.

It should be understood by those skilled in the art that obvious structural modifications, or usages, can be made without departing from the spirit or scope of the invention. For example, the portable C-arm support could be used for other fluoroscopy, beyond angio fluoroscopy; or, a gearing system could be substituted for the drive chain. Accordingly, reference should be made primarily to the appended Claims rather than the foregoing description to determine the spirit and scope of the invention.

I claim:

1. In a portable x-ray device of the type having an x-ray source, an image receptor, and a C-arm support apparatus, wherein a C-arm slides in a stationary arc in a single X-Y plane through a C-sleeve mounted on a portable base, the improvement comprising: a rotatable tilt bearing means for pivoting the arc, and C-sleeve, in a Z-plane around a pivot axis; and a sliding pivot point means for repositioning the tilt bearing means, and pivot axis, in the X-Y plane along an arcuate path from approximately a horizontal position, when the x-ray beam is vertical, to a position approximately 60 degrees below horizontal in a vertical plane.

2. In a portable x-ray device of the type having an x-ray source, an x-ray beam, an image receptor assembly, and a C-arm support apparatus, wherein a C-arm slides in an arc within a single plane through a fixed C-slider housing, and the C-arm and C-slider housing are mounted onto a base, the improvement comprising: a rotatable tilt bearing means for pivoting the C-slider housing in a rotational axis; the C-arm and C-slider housing are mounted onto the base by the rotatable tilt bearing means; and, a sliding pivot point means for selectively repositioning the rotational axis, and C-slider housing, along an arc from approximately a horizontal position, when the x-ray beam is vertical, to between a position approximately 60 degrees and 40 degrees below horizontal in a vertical plane.

3. The device of claim 2 wherein the base has wheels for portability; the rotatable tilt bearing means includes a rotatable tilt bearing; and the C-arm and C-slider housing are mounted onto the base by the rotatable tilt bearing.

4. The device of claim 3 wherein the tilt bearing means comprises a reversible drive motor, removably attached to the rotatable tilt bearing, to selectively rotate the C-slider housing about the C-slider pivot axis.

5. The device of claim 4 wherein the sliding pivot point means comprises: an arcuate pivot carriage guide track mounted to the base; a carriage with guide rollers which slides within the track, wherein the carriage is attached to the C-slider housing by a rotatable tilt bearing that rides atop a slot in the guide track.

6. The device of claim 5 wherein a drive gearmotor selectively locates the carriage and C-slider housing by a drive chain attached to the carriage.

7. In a portable x-ray device of the type having an x-ray source, an x-ray beam, an image receptor assembly, and a C-arm support apparatus, wherein a C-arm slides in an arc within a single plane through a fixed C-slider housing, and the C-arm and C-slider housing are mounted onto a base, the improvement comprising: a rotatable tilt bearing means for pivoting the C-slider housing in a rotational axis; the C-arm and C-slider housing are mounted onto the base by the rotatable tilt bearing means; and a sliding pivot point means for selectively repositioning the rotational axis, and C-slider housing, along an arc from approximately a horizontal position to a position between approximately 60 degrees and 40 degrees below horizontal in a vertical plane.

8. In a portable x-ray device of the type having an x-ray source, an x-ray beam, an image receptor assembly, and a C-arm support apparatus, wherein a C-arm slides in an arc within a single plane through a fixed C-slider housing, the C-arm and C-slider housing move only in a single plane relative to one another, and the C-arm and C-slider housing are mounted onto a wheeled base, the improvement comprising:
   a. a rotatable tilt bearing means for pivoting the C-slider housing in a rotational axis, wherein:
      i. the rotatable tilt bearing means includes a rotatable tilt bearing; and
      ii. the C-arm and C-slider housing are mounted onto the base by the rotatable tilt bearing.

* * * * *